(12) United States Patent
Han et al.

(10) Patent No.: US 9,957,614 B2
(45) Date of Patent: May 1, 2018

(54) RUTHENIUM COMPOUND, PREPARATION METHOD THEREFOR, PRECURSOR COMPOSITION FOR FILM DEPOSITION CONTAINING SAME, AND METHOD FOR DEPOSITING FILM BY USING SAME

(71) Applicant: UP CHEMICAL CO., LTD., Pyeongtaek-si (KR)

(72) Inventors: Won Seok Han, Pyeongtaek-si (KR); So Young Kim, Pyeongtaek-si (KR); Wonyong Koh, Daejeon (KR)

(73) Assignee: UP Chemical Co., Ltd., Pyeongtaek-si (KR)

( * ) Notice: Subject to any disclaimer, the term of this patent is extended or adjusted under 35 U.S.C. 154(b) by 0 days. days.

(21) Appl. No.: 15/314,839

(22) PCT Filed: May 26, 2015

(86) PCT No.: PCT/KR2015/005232
§ 371 (c)(1),
(2) Date: Nov. 29, 2016

(87) PCT Pub. No.: WO2015/182946
PCT Pub. Date: Dec. 3, 2015

(65) Prior Publication Data
US 2017/0226638 A1 Aug. 10, 2017

(30) Foreign Application Priority Data

May 30, 2014 (KR) .................... 10-2014-0065854
Nov. 21, 2014 (KR) .................... 10-2014-0163832

(51) Int. Cl.
C07F 15/00 (2006.01)
C23C 16/455 (2006.01)
(Continued)

(52) U.S. Cl.
CPC .... C23C 16/45525 (2013.01); C07F 15/0046 (2013.01); C09D 1/00 (2013.01); C23C 16/06 (2013.01)

(58) Field of Classification Search
None
See application file for complete search history.

(56) References Cited

U.S. PATENT DOCUMENTS

2013/0062768 A1 3/2013 Waechtler et al.

FOREIGN PATENT DOCUMENTS

CN 101356181 B 1/2012
CN 102639548 A 8/2012
(Continued)

OTHER PUBLICATIONS

Pelletier, Journal of Medicinal Chemistry, 2010, V53, 19, p. 6923-6933.*

(Continued)

*Primary Examiner* — Joseph A Miller, Jr.
(74) *Attorney, Agent, or Firm* — Greer, Burns & Crain, Ltd.

(57) ABSTRACT

The present disclosure relates to a novel ruthenium compound, a method for preparing the ruthenium compound, a precursor composition for depositing a ruthenium-containing film including the ruthenium compound, and a method for depositing a ruthenium-containing film by using the precursor composition.

12 Claims, 13 Drawing Sheets

(51) Int. Cl.
*C09D 1/00* (2006.01)
*C23C 16/06* (2006.01)

(56) References Cited

FOREIGN PATENT DOCUMENTS

| | | |
|---|---|---|
| JP | 2005-232142 A | 9/2005 |
| JP | 2008-094728 A | 4/2008 |
| JP | 2008-266329 A | 11/2008 |
| KR | 10-2009-0082543 | 7/2009 |
| KR | 10-2010-0060482 | 6/2010 |
| KR | 10-2012-0012319 | 2/2012 |
| KR | 10-2012-0085892 | 8/2012 |
| KR | 10-2013-0043557 | 4/2013 |
| KR | 10-2014-0131219 | 11/2014 |
| TW | 201317245 A1 | 5/2013 |
| WO | WO 2008/044478 A1 | 4/2008 |

OTHER PUBLICATIONS

Ekectrochemical and Solid State Letters, 2009, V12 (11), p. D85-88.*
Korean office action, KIPRIS (Year: 2017).*
Response to Korean Office Action, Applicant (Year: 2017).*
KR2010060482MT Jun. 2010 Shin, eng machine translation (Year: 2010).*
Int'l. Search Report of PCT/KR2015/005232 dated Jul. 9, 2015.
Sung-Soo Yim et al., "Nucleation kinetics of Ru on silicon oxide and silicon nitride surfaces deposited by atomic layer deposition", Journal of Applied Physics, vol. 103, 113509, Jun. 10, 2008.
Seong Keun Kim et al., "Investigation on the Growth Initiation of Ru Thin Films by Atomic Layer Deposition", Chemistry of Materials, vol. 22, pp. 2850-2856, Apr. 13, 2010.

* cited by examiner

RUTHENIUM COMPOUND, PREPARATION METHOD THEREFOR, PRECURSOR COMPOSITION FOR FILM DEPOSITION CONTAINING SAME, AND METHOD FOR DEPOSITING FILM BY USING SAME

TECHNICAL FIELD

The invention relates to a novel ruthenium compound, a method for preparing the ruthenium compound, a precursor composition for depositing a film containing the ruthenium compound, and a method for depositing a film by using the precursor composition.

BACKGROUND

Ruthenium metal is excellent in thermal and chemical stability and also has a low resistivity ($\rho_{bulk}$=7.6 $\mu\Omega\cdot$cm) and a high work function ($F_{bulk}$=4.71 eV) and thus can be used as a gate electrode of a transistor or a capacitor electrode material of a DRAM or FeRAM. Particularly, in case of using oxides containing titanium, such as $TiO_2$, STO (Sr-$TiO_3$), BST [(Ba, Sr)$TiO_3$], and the like, as a source for a high dielectric material of a next-generation DRAM capacitor, it is necessary to use a ruthenium electrode in order to minimize a leakage current.

The ruthenium metal has an excellent adhesion to copper metal and has difficulty in forming a solid solution with Cu, and, thus, application of the ruthenium metal as a seed layer for a Cu wiring process using electroplating in a semiconductor manufacturing process is being actively studied.

Meanwhile, a ruthenium oxide ($RuO_2$) is also a conductive material having a low resistivity ($\rho_{bulk}$=46 $\mu\Omega\cdot$cm) and an excellent thermal stability even at 800° C. and thus highly likely to be applied as a lower electrode of a metal-insulator-metal (MIM) capacitor in the future.

In order to use the ruthenium metal and the ruthenium oxide as a capacitor electrode of extremely miniaturized next-generation electronic devices, particularly a DRAM (Dynamic Random Access Memory) having a high aspect ratio, it is necessary to apply an organic metal chemical vapor deposition method or an atomic layer deposition method that enables an excellent step coverage on a seriously uneven surface, and, thus, a ruthenium precursor compound suitable therefor is needed.

When a ruthenium metal film or oxide film is formed using the atomic layer deposition method, a bis(ethylcyclopentadienyl)ruthenium [(EtCp)$_2$Ru] precursor compound and an oxygen-containing gas are usually used. However, (EtCp)$_2$Ru is a liquid at room temperature and has a high vapor pressure, but the atomic layer deposition method using the (EtCp)$_2$Ru precursor compound has a problem that particularly initial film growth is very slow. On a silicon oxide film or a silicon nitride film, 100 or more gas supply cycles (incubation cycles) are needed until film growth per gas supply cycle of the atomic layer deposition method can be obtained to a certain degree. The atomic layer deposition method using the (EtCp)$_2$Ru precursor compound also has a defect of slow film growth per source supply cycle (lower than 0.05 nm/cycle) ["Nucleation kinetics of Ru on silicon oxide and silicon nitride surfaces deposited by atomic layer deposition", Journal of Applied Physics, volume 103, 113509 (2008)].

It has also been known that 2,4-(dimethylpentadienyl)(ethylcyclopentadienyl)Ru (DER) which is a liquid at room temperature and has a relatively high vapor pressure and an oxygen-containing gas are used in the atomic layer deposition method, but it has been reported that in the atomic layer deposition method using the DER, an incubation cycle is needed 100 or 200 times on a titanium oxide ($TiO_2$) or titanium nitride (TiN) substrate, and it has been known that film growth per source supply cycle is only 0.034 nm/cycle ["Investigation on the Growth Initiation of Ru Thin Films by Atomic Layer Deposition", Chemistry of Materials, volume 22, 2850-2856 (2010)].

Accordingly, a ruthenium precursor compound that enables fast initial film growth during atomic layer deposition or chemical vapor deposition and particularly fast film growth per gas supplying cycle in the atomic layer deposition method.

DISCLOSURE OF THE INVENTION

Problems to be Solved by the Invention

Accordingly, the present disclosure provides a novel ruthenium compound, a method for preparing the ruthenium compound, a precursor composition for depositing a film containing the ruthenium compound, and a method for depositing a film by using the precursor composition.

However, problems to be solved by the present disclosure are not limited to the above-described problems. Although not described herein, other problems to be solved by the present disclosure can be clearly understood by those skilled in the art from the following descriptions.

Means for Solving the Problems

In accordance with a first aspect of the present disclosure, there is provided a ruthenium compound represented by the following Chemical Formula 1:

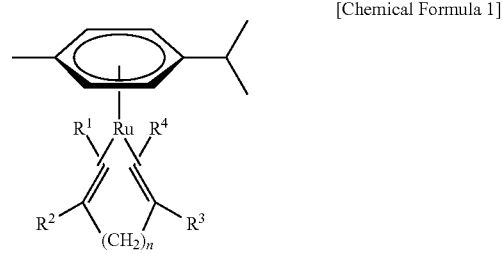

[Chemical Formula 1]

in the above Chemical Formula 1, each of $R^1$ to $R^4$ independently includes H, or a linear or branched $C_{1-5}$ alkyl group, and n is an integer of from 0 to 3.

In accordance with a second aspect of the present disclosure, there is provided a method for preparing a ruthenium compound, including reacting a mixture including a [RuX$_2$ (p-cymene)]$_2$ compound represented by the following Chemical Formula 2, a carbonate salt of an alkali metal represented as $M_2CO_3$, and a diene neutral ligand represented by the following Chemical Formula 3 in an organic solvent including a primary alcohol or secondary alcohol having 5 or less carbon atoms, as shown in the following Reaction Formula 1, to obtain a ruthenium compound represented by the following Chemical Formula 1:

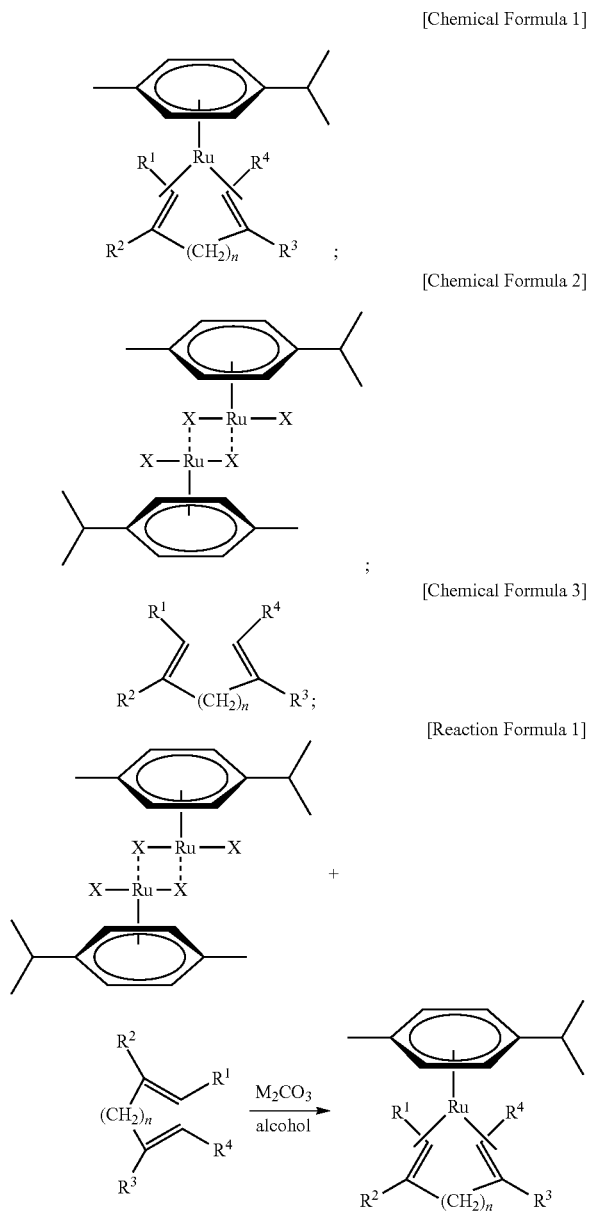

wherein in the above Formulas,

M includes Li, Na, or K,

X includes Cl, Br, or I, and each of $R^1$ to $R^4$ independently includes H, or a linear or branched $C_{1-5}$ alkyl group, and n is an integer of from 0 to 3.

In accordance with a third aspect of the present disclosure, there is provided a precursor composition for depositing a ruthenium-containing film, including the ruthenium compound according to the first aspect of the present disclosure.

In accordance with a fourth aspect of the present disclosure, there is provided a method for depositing a ruthenium-containing film, including depositing a ruthenium-containing film according to the third aspect of the present disclosure to form a ruthenium-containing film by using a precursor composition.

Effects of the Invention

According to an exemplary embodiment of the present disclosure, it is possible to provide a ruthenium compound and a method for preparing the ruthenium compound which enables faster initial film growth than a conventional ruthenium precursor compound used as a precursor for an atomic layer deposition method or a chemical vapor deposition method and also enables much faster film formation per source gas supply cycle of the atomic layer deposition. The novel ruthenium compound according to an exemplary embodiment of the present disclosure can be used for forming a ruthenium-containing film or thin film and can be easily mass-produced from a commercially available source material.

According to an exemplary embodiment of the present disclosure, in case of forming a ruthenium-containing film by an atomic layer deposition method using the ruthenium compound, a ruthenium-containing film having a high electric conductivity with a smooth surface can be formed. The atomic layer deposition method using the ruthenium compound according to an exemplary embodiment of the present disclosure enables fast initial film growth and takes less time to form a ruthenium-containing film to a required thickness as compared with the conventionally known atomic layer deposition method. Therefore, if the ruthenium compound according to an exemplary embodiment of the present disclosure is applied to a semiconductor production process for preparing a ruthenium-containing film, it is expected that productivity of a film-forming apparatus will increase.

MODE FOR CARRYING OUT THE INVENTION

Figure 1:
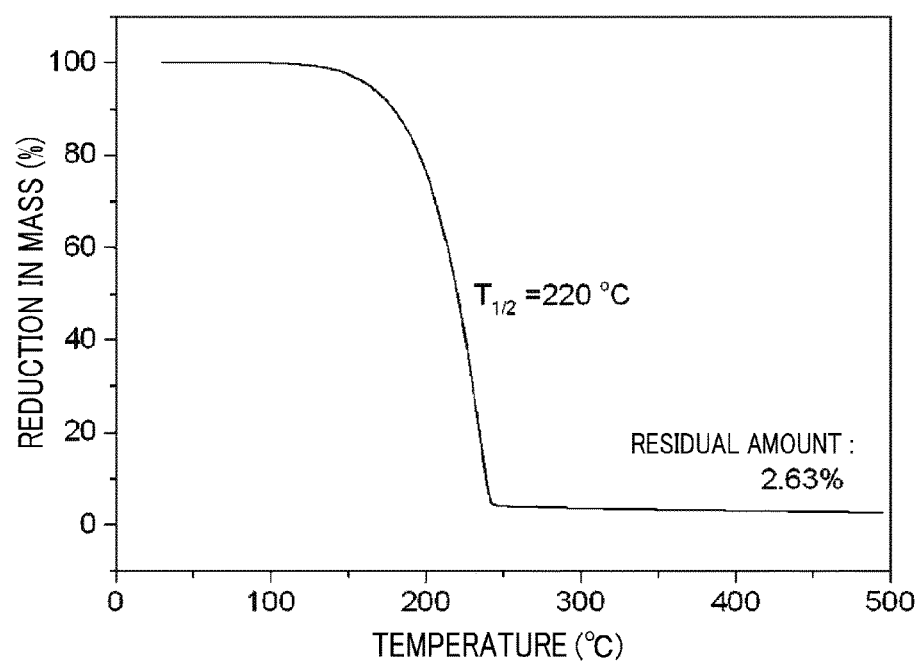
FIG. 1 is a thermogravimetric analysis graph of the ruthenium compound prepared in accordance with Example 1 of the present disclosure.
Figure 2:
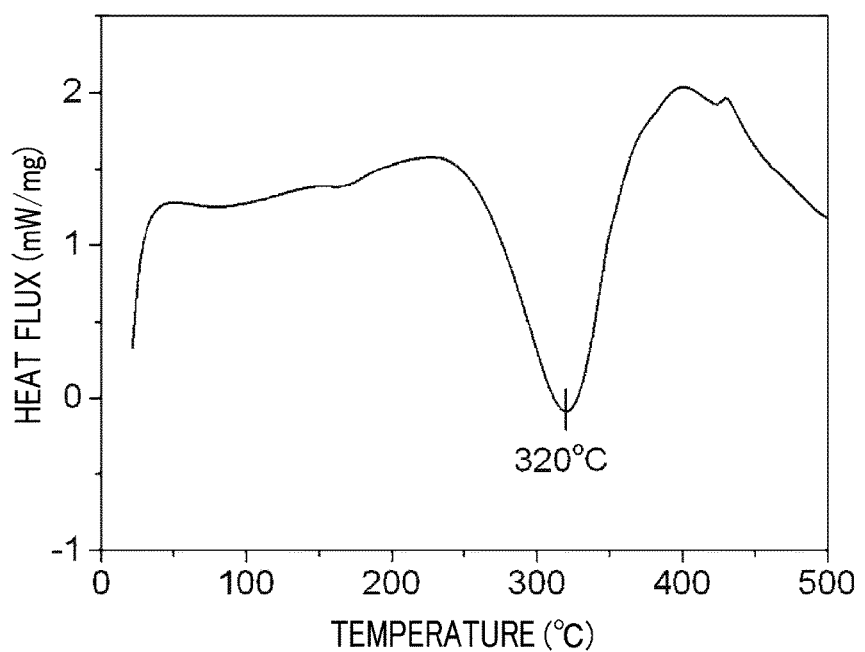
FIG. 2 is a differential scanning calorimetric analysis graph of the ruthenium compound prepared in accordance with Example 1 of the present disclosure.
Figure 3:
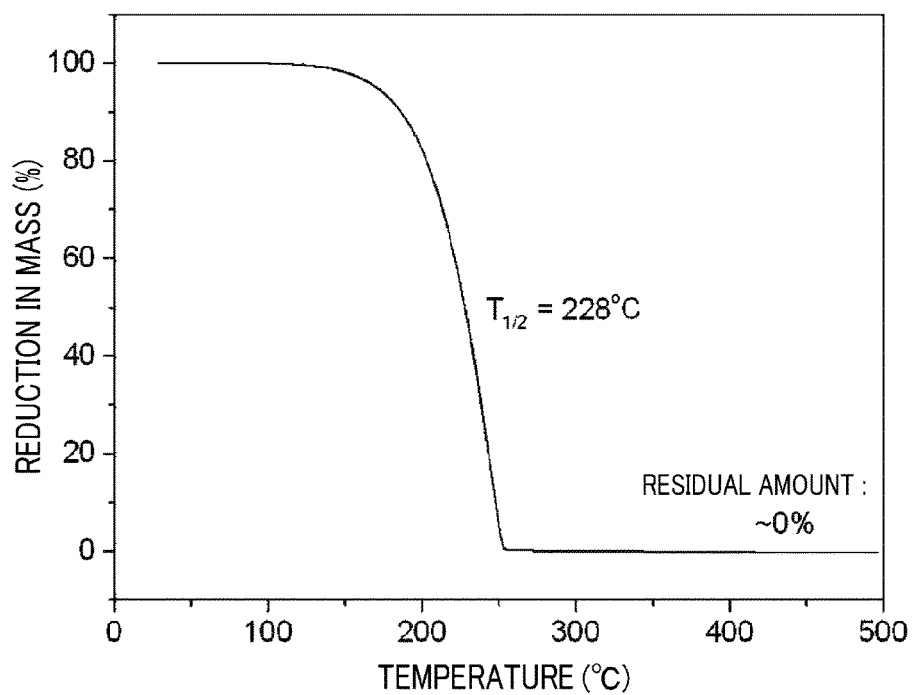
FIG. 3 is a thermogravimetric analysis graph of the ruthenium compound prepared in accordance with Example 2 of the present disclosure.
Figure 4:
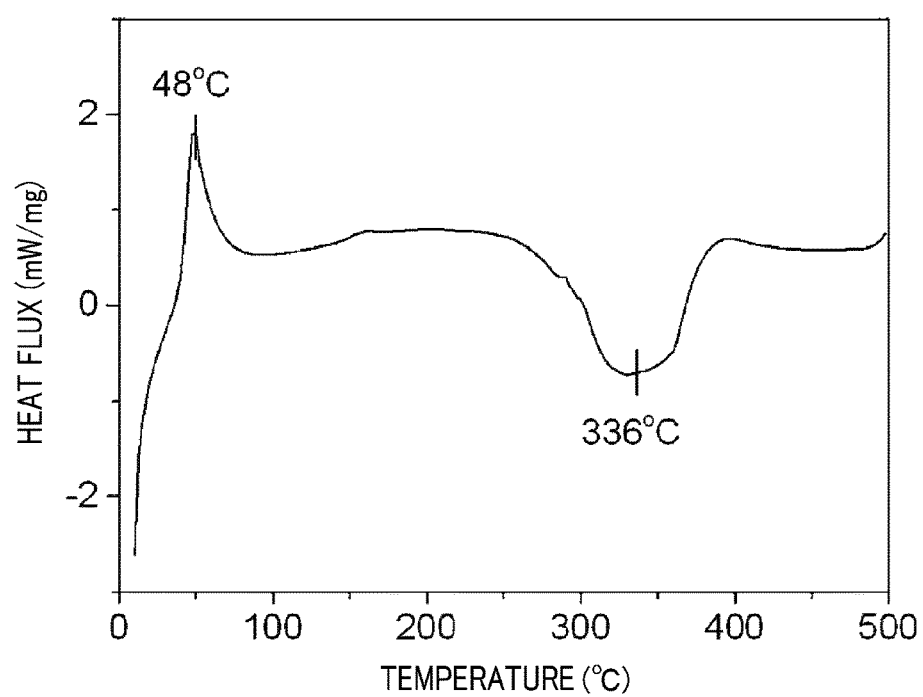
FIG. 4 is a differential scanning calorimetric analysis graph of the ruthenium compound prepared in accordance with Example 2 of the present disclosure.
Figure 5:
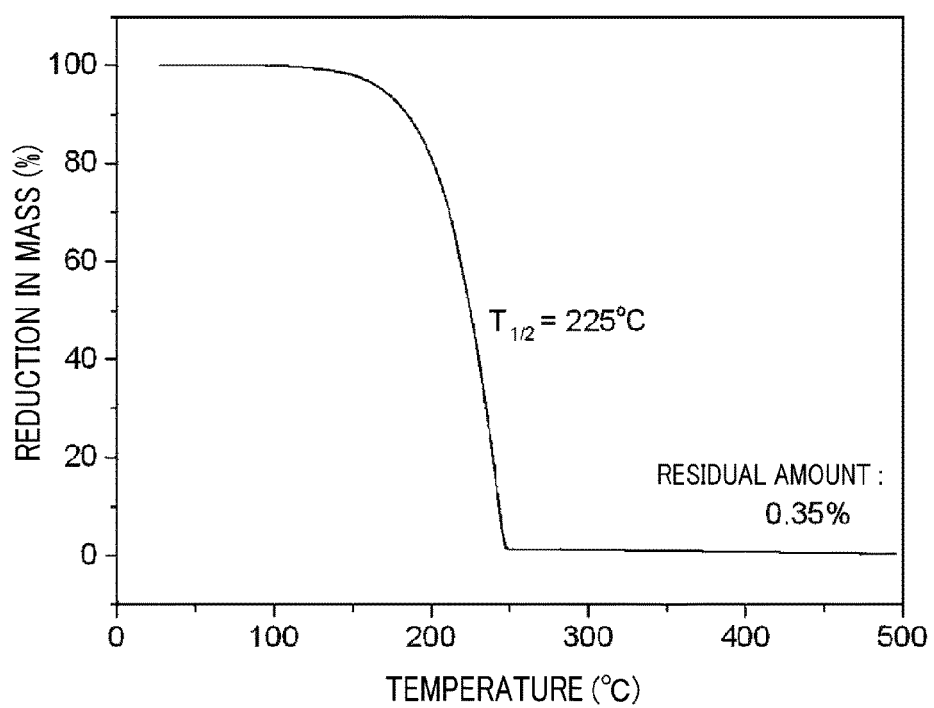
FIG. 5 is a thermogravimetric analysis graph of the ruthenium compound prepared in accordance with Example 3 of the present disclosure.
Figure 6:
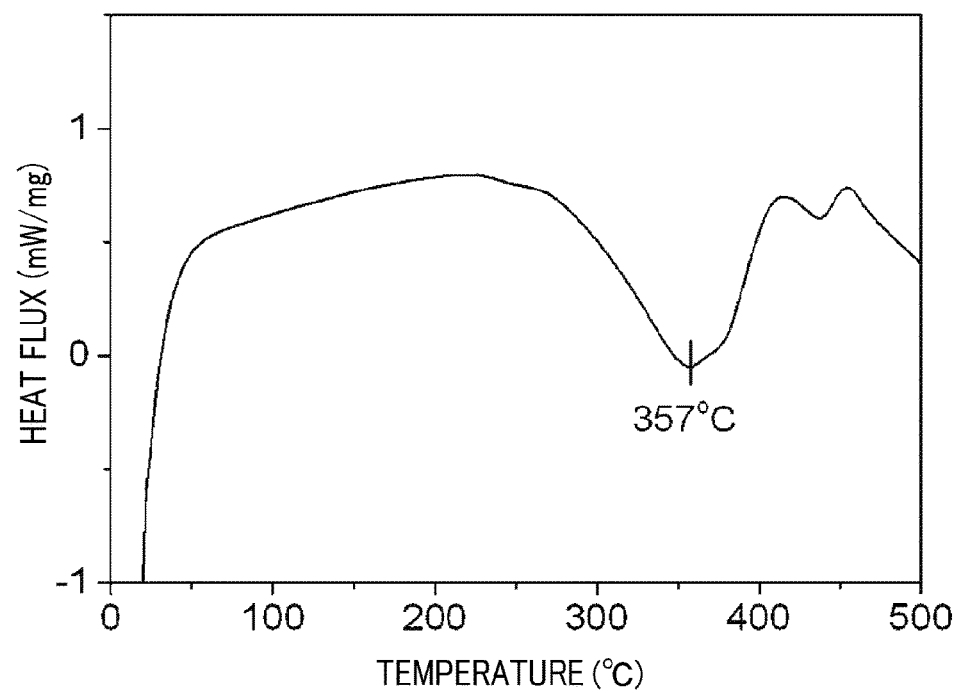
FIG. 6 is a differential scanning calorimetric analysis graph of the ruthenium compound prepared in accordance with Example 3 of the present disclosure.
Figure 7:
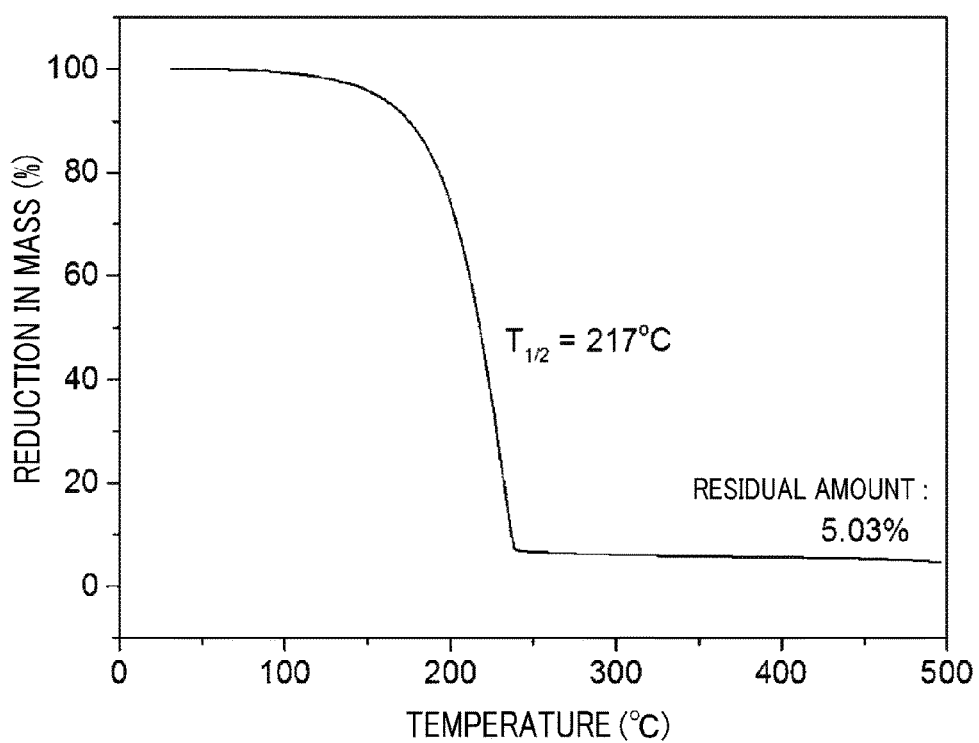
FIG. 7 is a thermogravimetric analysis graph of the ruthenium compound prepared in accordance with Example 4 of the present disclosure.
Figure 8:
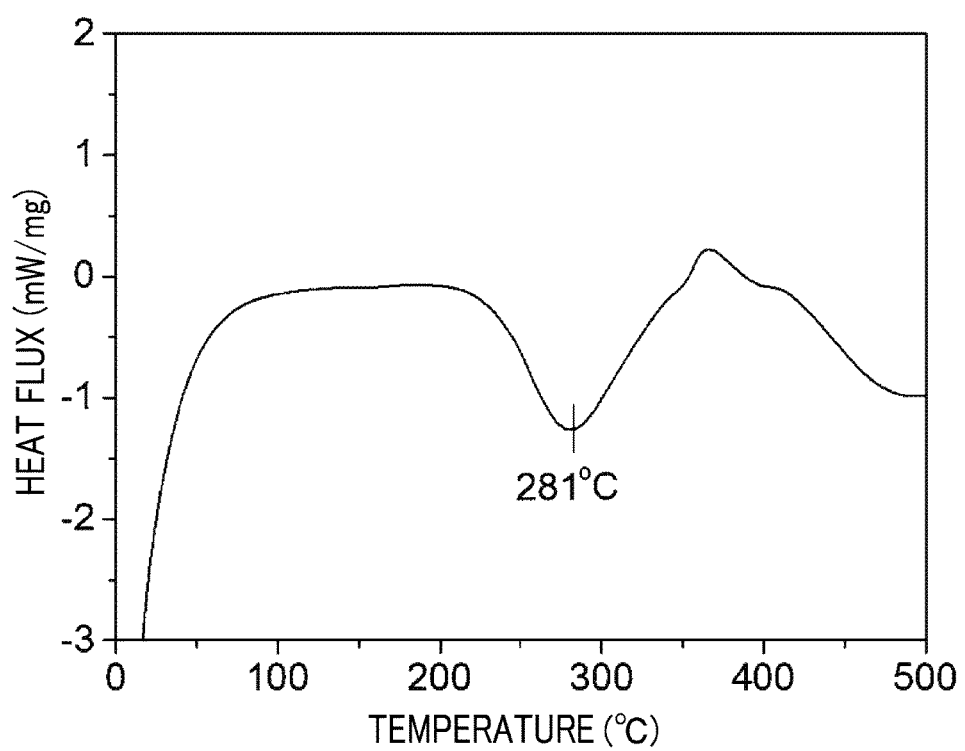
FIG. 8 is a differential scanning calorimetric analysis graph of the ruthenium compound prepared in accordance with Example 4 of the present disclosure.

Hereinafter, examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the another element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party.

Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, the term "alkyl group" may individually include a linear or branched saturated $C_{1-10}$ or $C_{1-5}$ alkyl group, and may include, for example, methyl, ethyl, propyl, butyl, pentyl, hexyl, heptyl, octyl, nonyl, decyl, or all the possible isomers thereof, but may not be limited thereto.

Through the whole document, the term "alkali metal" refers to metal included in Group 1 of the Periodic Table and may be Li, Na, K, Rb, or Cs, but may not be limited thereto.

Through the whole document, the term "neutral ligand" refers to a hydrocarbon compound including one double bond or two or more double bonds or triple bonds and may include a member selected from the group consisting of a linear, branched, or open-ring $C_{1-10}$ alkyne; a linear, branched, or open-ring $C_{1-10}$ alkene; a linear, branched, or open-ring $C_{1-10}$ diene; and a linear, branched, or open-ring $C_{1-10}$ triene, but may not be limited thereto.

Hereinafter, the exemplary embodiments of the present disclosure will be described in detail, but the present disclosure may not be limited thereto.

In accordance with a first aspect of the present disclosure, there is provided a ruthenium compound represented by the following Chemical Formula 1:

[Chemical Formula 1]

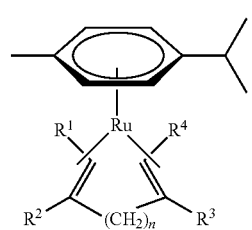

in the above Chemical Formula 1,
each of $R^1$ to $R^4$ independently includes H, or a linear or branched $C_{1-5}$ alkyl group, and
n is an integer of from 0 to 3.

In an exemplary embodiment of the present disclosure, the linear or branched $C_{1-5}$ alkyl group may include a member selected from the group consisting of methyl group, ethyl group, n-propyl group, iso-propyl group, n-butyl group, iso-butyl group, sec-butyl group, tert-butyl group, n-pentyl group, iso-pentyl group, sec-pentyl group, tert-pentyl group, neo-pentyl group, 3-pentyl group, and isomers thereof, but may not be limited thereto.

In an exemplary embodiment of the present disclosure, n may be 0, and each of $R^1$ to $R^4$ independently may include H; or a member selected from the group consisting of methyl group, ethyl group, iso-propyl group, and tert-butyl group, but may not be limited thereto.

A ruthenium compound in accordance with an exemplary embodiment of the present disclosure may include a member selected from the group consisting of (p-cymene){CH$_2$=CHCH=CH$_2$}Ru, (p-cymene){MeCH=CHCH=CH$_2$}Ru, (p-cymene){EtCH=CHCH=CH$_2$}Ru, (p-cymene){$^n$PrCH=CHCH=CH$_2$}Ru, (p-cymene){$^i$PrCH=CHCH=CH$_2$}Ru, (p-cymene){$^n$BuCH=CHCH=CH$_2$}Ru, (p-cymene){$^i$BuCH=CHCH=CH$_2$}Ru, (p-cymene){$^{sec}$BuCH=CHCH=CH$_2$}Ru, (p-cymene){$^t$BuCH=CHCH=CH$_2$}Ru, (p-cymene){(n-pentyl)CH=CHCH=CH$_2$}Ru, (p-cymene){(iso-pentyl)CH=CHCH=CH$_2$}Ru, (p-cymene){(sec-pentyl)CH=CHCH=CH$_2$}Ru, (p-cymene){(neo-pentyl)CH=CHCH=CH$_2$}Ru, (p-cymene){(tert-pentyl)CH=CHCH=CH$_2$}Ru, (p-cymene){(3-pentyl)CH=CHCH=CH$_2$}Ru, (p-cymene){CH$_2$=C(Me)CH=CH$_2$}Ru, (p-cymene){CH$_2$=C(Et)CH=CH$_2$}Ru, (p-cymene){CH$_2$=C(nPr)CH=CH$_2$}Ru, (p-cymene)

{CH₂=C(ⁱPr)CH=CH₂}Ru, (p-cymene){CH₂=C(nBu)CH=CH₂}Ru, (p-cymene){CH₂=C(ᵗBu)CH=CH₂}Ru, (p-cymene){CH₂=C(ˢᵉᶜBu)CH=CH₂}Ru, (p-cymene){CH₂=C(ⁿBu)CH=CH₂}Ru, (p-cymene){CH₂=C(n-pentyl)CH=CH₂}Ru, (p-cymene){CH₂=C(iso-pentyl)CH=CH₂}Ru, (p-cymene){CH₂=C(sec-pentyl)CH=CH₂}Ru, (p-cymene){CH₂=C(neo-pentyl)CH=CH₂}Ru, (p-cymene){CH₂=C(tert-pentyl)CH=CH₂}Ru, (p-cymene){CH₂=C(3-pentyl)CH=CH₂}Ru, (p-cymene){MeCH=CHCH=CHMe}Ru, (p-cymene){EtCH=CHCH=CHEt}Ru, (p-cymene){nPrCH=CHCH=CHⁿPr}Ru, (p-cymene){ⁱPrCH=CHCH=CHⁱPr}Ru, (p-cymene){ⁿBuCH=CHCH=CHⁿBu}Ru, (p-cymene){ⁱBuCH=CHCH=CHⁱBu}Ru, (p-cymene){ˢᵉᶜBuCH=CHCH=CHˢᵉᶜBu}Ru, (p-cymene){ᵗBuCH=CHCH=CHᵗBu}Ru, (p-cymene){(n-pentyl)CH=CHCH=CH(n-pentyl)}Ru, (p-cymene){(iso-pentyl)CH=CHCH=CH(iso-pentyl)}Ru, (p-cymene){(sec-pentyl)CH=CHCH=CH(sec-pentyl)}Ru, (p-cymene){(neopentyl)CH=CHCH=CH(neo-pentyl)}Ru, (p-cymene){(tert-pentyl)CH=CHCH=CH(tert-pentyl)}Ru, (p-cymene){(3-pentyl)CH=CHCH=CH(3-pentyl)}Ru, (p-cymene){CH₂=C(Me)C(Me)=CH₂}Ru, (p-cymene){CH₂=C(Et)C(Et)=CH₂}Ru, (p-cymene){CH₂=C(nPr)C(nPr)=CH₂}Ru, (p-cymene){CH₂=C(ⁱPr)C(ⁱPr)=CH₂}Ru, (p-cymene){CH₂=C(ⁿBu)C(ⁿBu)=CH₂}Ru, (p-cymene){CH₂=C(ⁱBu)C(ⁱBu)=CH₂}Ru, (p-cymene){CH₂=C(ˢᵉᶜBu)C(ˢᵉᶜBu)=CH₂}Ru, (p-cymene){CH₂=C(ᵗBu)C(ᵗBu)=CH₂}Ru, (p-cymene){CH₂=C(n-pentyl)C(n-pentyl)=CH₂}Ru, (p-cymene){CH₂=C(iso-pentyl)C(iso-pentyl)=CH₂}Ru, (p-cymene){CH₂=C(sec-pentyl)C(sec-pentyl)=CH₂}Ru, (p-cymene){CH₂=C(neopentyl)C(neopentyl)=CH₂}Ru, (p-cymene){CH₂=C(tert-pentyl)C(tert-pentyl)=CH₂}Ru, (p-cymene){CH₂=C(3-pentyl)C(3-pentyl)=CH₂}Ru, (p-cymene){MeCH=C(Me)CH=CH₂}Ru, (p-cymene){MeCH=CHC(Me)=CH₂}Ru, (p-cymene){MeCH=C(Et)CH=CH₂}Ru, (p-cymene){MeCH=CHC(Et)=CH₂}Ru, (p-cymene){MeCH=CHCH=CHEt}Ru, (p-cymene){MeCH=C(ⁿPr)CH=CH₂}Ru, (p-cymene){MeCH=CHC(ⁿPr)=CH₂}Ru, (p-cymene){MeCH=CHCH=CHⁿPr}Ru, (p-cymene){MeCH=C(ⁱPr)CH=CH₂}Ru, (p-cymene){MeCH=CHC(ⁱPr)=CH₂}Ru, (p-cymene){MeCH=CHCH=CHⁱPr}Ru, (p-cymene){MeCH=C(ⁿBu)CH=CH₂}Ru, (p-cymene){MeCH=CHC(ⁿBu)=CH₂}Ru, (p-cymene){MeCH=CHCH=CHⁿBu}Ru, (p-cymene){MeCH=C(ⁱBu)CH=CH₂}Ru, (p-cymene){MeCH=CHC(ⁱBu)=CH₂}Ru, (p-cymene){MeCH=CHCH=CHⁱBu}Ru, (p-cymene){MeCH=C(ˢᵉᶜBu)CH=CH₂}Ru, (p-cymene){MeCH=CHC(ˢᵉᶜBu)=CH₂}Ru, (p-cymene){MeCH=CHCH=CHˢᵉᶜBu}Ru, (p-cymene){MeCH=C(ᵗBu)CH=CH₂}Ru, (p-cymene){MeCH=CHC(ᵗBu)=CH₂}Ru, (p-cymene){MeCH=CHCH=CHᵗBu}Ru, (p-cymene){EtCH=C(Me)CH=CH₂}Ru, (p-cymene){EtCH=CHC(Me)=CH₂}Ru, (p-cymene){EtCH=C(Et)CH=CH₂}Ru, (p-cymene){EtCH=CHC(Et)=CH₂}Ru, (p-cymene){EtCH=C(ⁿPr)CH=CH₂}Ru, (p-cymene){EtCH=CHC(ⁿPr)=CH₂}Ru, (p-cymene){EtCH=CHCH=CHⁿPr}Ru, (p-cymene){EtCH=C(ⁱPr)CH=CH₂}Ru, (p-cymene){EtCH=CHC(ⁱPr)=CH₂}Ru, (p-cymene){EtCH=CHCH=CHⁱPr}Ru, (p-cymene){EtCH=C(ⁿBu)CH=CH₂}Ru, (p-cymene){EtCH=CHC(ⁿBu)=CH₂}Ru, (p-cymene){EtCH=CHCH=CHⁿBu}Ru, (p-cymene){EtCH=C(ⁱBu)CH=CH₂}Ru, (p-cymene){EtCH=CHC(ⁱBu)=CH₂}Ru, (p-cymene){EtCH=CHCH=CHⁱBu}Ru, (p-cymene){EtCH=C(ˢᵉᶜBu)CH=CH₂}Ru, (p-cymene){EtCH=CHC(ˢᵉᶜBu)=CH₂}Ru, (p-cymene){EtCH=CHCH=CHˢᵉᶜBu}Ru, (p-cymene){EtCH=C(ᵗBu)CH=CH₂}Ru, (p-cymene){EtCH=CHC(ᵗBu)=CH₂}Ru, (p-cymene){EtCH=CHCH=CHᵗBu}Ru, (p-cymene){ⁱPrCH=C(Me)CH=CH₂}Ru, (p-cymene){ⁱPrCH=CHC(Me)=CH₂}Ru, (p-cymene){ⁱPrCH=CHCH=CHMe}Ru, (p-cymene){ⁱPrCH=C(Et)CH=CH₂}Ru, (p-cymene){ⁱPrCHCH=CHC(Et)=CH₂}Ru, (p-cymene){ⁱPrCH=CHCH=CHEt}Ru, (p-cymene){ⁱPrCH=C(ⁿPr)CH=CH₂}Ru, (p-cymene){ⁱPrCH=CHC(ⁿPr)=CH₂}Ru, (p-cymene){ⁱPrCH=CHCH=CHⁿPr}Ru, (p-cymene){ⁱPrCH=C(ⁱPr)CH=CH₂}Ru, (p-cymene){ⁱPrCH=CHC(ⁱPr)=CH₂}Ru, (p-cymene){ⁱPrCH=C(ⁿBu)CH=CH₂}Ru, (p-cymene){ⁱPrCH=CHC(ⁿBu)=CH₂}Ru, (p-cymene){ⁱPrCH=CHCH=CHⁿBu}Ru, (p-cymene){ⁱPrCH=C(ⁱBu)CH=CH₂}Ru, (p-cymene){ⁱPrCH=CHC(ⁱBu)=CH₂}Ru, (p-cymene){ⁱPrCHCH=CHCH=CHⁱBu}Ru, (p-cymene){ⁱPrCH=C(ˢᵉᶜBu)CH=CH₂}Ru, (p-cymene){ⁱPrCH=CHC(ˢᵉᶜBu)=CH₂}Ru, (p-cymene){ⁱPrCH=CHCH=CHˢᵉᶜBu}Ru, (p-cymene){ⁱPrCH=C(ᵗBu)CH=CH₂}Ru, (p-cymene){ⁱPrCH=CHC(ᵗBu)=CH₂}Ru, (p-cymene){ⁱPrCH=CHCH=CHᵗBu}Ru, (p-cymene){ᵗBuCH=C(Me)CH=CH₂}Ru, (p-cymene){ᵗBuCH=CHC(Me)=CH₂}Ru, (p-cymene){ᵗBuCH=CHCH=CHMe}Ru, (p-cymene){ᵗBuCH=C(Et)CH=CH₂}Ru, (p-cymene){ᵗBuCH=CHC(Et)=CH₂}Ru, (p-cymene){ᵗBuCH=CHCH=CHEt}Ru, (p-cymene){ᵗBuCH=C(ⁿPr)CH=CH₂}Ru, (p-cymene){ᵗBuCH=CHC(ⁿPr)=CH₂}Ru, (p-cymene){ᵗBuCH=CHCH=CHⁿPr}Ru, (p-cymene){ᵗBuCH=C(ⁱPr)CH=CH₂}Ru, (p-cymene){ᵗBuCH=CHC(ⁱPr)=CH₂}Ru, (p-cymene){ᵗBuCH=CHCH=CHⁱPr}Ru, (p-cymene){ᵗBuCH=C(ⁿBu)CH=CH₂}Ru, (p-cymene){ᵗBuCH=CHC(ⁿBu)=CH₂}Ru, (p-cymene){ᵗBuCH=CHCH=CHⁿBu}Ru, (p-cymene){ᵗBuCH=C(ⁱBu)CH=CH₂}Ru, (p-cymene){ᵗBuCH=CHC(ⁱBu)=CH₂}Ru, (p-cymene){ᵗBuCH=CHCH=CHⁱBu}Ru, (p-cymene){ᵗBuCH=C(ˢᵉᶜBu)CH=CH₂}Ru, (p-cymene){ᵗBuCH=CHC(ˢᵉᶜBu)=CH₂}Ru, (p-cymene){ᵗBuCH=CHCH=CHˢᵉᶜBu}Ru, (p-cymene){ᵗBuCH=C(ᵗBu)CH=CH₂}Ru, (p-cymene){ᵗBuCH=CHC(ᵗBu)=CH₂}Ru, (p-cymene){CH₂=CHCH₂CH=CH₂}Ru, (p-cymene){MeCH=CHCH₂CH=CH₂}Ru, (p-cymene){EtCH=CHCH₂CH=CH₂}Ru, (p-cymene){ⁿPrCH=CHCH₂CH=CH₂}Ru, (p-cymene){ⁱPrCH=CHCH₂CH=CH₂}Ru, (p-cymene){ⁿBuCH=CHCH₂CH=CH₂}Ru, (p-cymene){ⁱBuCH=CHCH₂CH=CH₂}Ru, (p-cymene){ˢᵉᶜBuCH=CHCH₂CH=CH₂}Ru, (p-cymene){ᵗBuCH=CHCH₂CH=CH₂}Ru, (p-cymene){(n-pentyl)CH=CHCH₂CH=CH₂}Ru, (p-cymene){(iso-pentyl)CH=CHCH₂CH=CH₂}Ru, (p-cymene){(sec-pentyl)CH=CHCH₂CH=CH₂}Ru, (p-cymene){(neo-pentyl)CH=CHCH₂CH=CH₂}Ru, (p-cymene){(tert-pentyl)CH=CHCH₂CH=CH₂}Ru, (p-cymene){(3-pentyl)CH=CHCH₂CH=CH₂}Ru, (p-cymene){CH₂=C(Me)CH₂CH=CH₂}Ru, (p-cymene){CH₂=C(Et)CH₂CH=CH₂}Ru, (p-cymene){CH₂=C(ⁿPr)CH₂CH=CH₂}Ru, (p-cymene){CH₂=C(ⁱPr)CH₂CH=CH₂}Ru, (p-cymene){CH₂=C(ⁿBu)CH₂CH=CH₂}Ru, (p-cymene){CH₂=C(ⁱBu)CH₂CH=CH₂}Ru, (p-cymene){CH₂=C(ˢᵉᶜBu)CH₂CH=CH₂}Ru, (p-cymene){CH₂=C(ᵗBu)

CH₂CH=CH₂}Ru, (p-cymene){CH₂=C(n-pentyl)
CH₂CH=CH₂}Ru, (p-cymene){CH₂=C(iso-pentyl)
CH₂CH=CH₂}Ru, (p-cymene){CH₂=C(sec-pentyl)
CH₂CH=CH₂}Ru, (p-cymene){CH₂=C(neo-pentyl)
CH₂CH=CH₂}Ru, (p-cymene){CH₂=C(tert-pentyl)
CH₂CH=CH₂}Ru, (p-cymene){CH₂=C(3-pentyl)
CH₂CH=CH₂}Ru, (p-cymene){CH₂=CH(CH₂)₂
CH=CH₂}Ru, (p-cymene){MeCH=CH(CH₂)₂
CH=CH₂}Ru, (p-cymene){EtCH=CH(CH₂)₂
CH=CH₂}Ru, (p-cymene){nPrCH=CH(CH₂)₂
CH=CH₂}Ru, (p-cymene){ⁱPrCH=CH(CH₂)₂
CH=CH₂}Ru, (p-cymene){ⁿBuCH=CH(CH₂)₂
CH=CH₂}Ru, (p-cymene){ⁱBuCH=CH(CH₂)₂
CH=CH₂}Ru, (p-cymene){ˢᵉᶜBuCH=CH(CH₂)₂
CH=CH₂}Ru, (p-cymene){ᵗBuCH=CH(CH₂)₂
CH=CH₂}Ru, (p-cymene){(n-pentyl)CH=CH(CH₂)₂
CH=CH₂}Ru, (p-cymene){(iso-pentyl)CH=CH(CH₂)₂
CH=CH₂}Ru, (p-cymene){(sec-pentyl)CH=CH(CH₂)₂
CH=CH₂}Ru, (p-cymene){(neopentyl)CH=CH(CH₂)₂
CH=CH₂}Ru, (p-cymene){(tert-pentyl)CH=CH(CH₂)₂
CH=CH₂}Ru, (p-cymene){CH₂=CH(CH₂)₂
CH=CH₂}Ru, (p-cymene){CH₂=C(Me)(CH₂)₂
CH=CH₂}Ru, (p-cymene){CH₂=C(Et)(CH₂)₂
CH=CH₂}Ru, (p-cymene){CH₂=C(ⁿPr)(CH₂)₂
CH=CH₂}Ru, (p-cymene){CH₂=C(ⁱPr)(CH₂)₂
CH=CH₂}Ru, (p-cymene){CH₂=C(ⁿBu)(CH₂)₂
CH=CH₂}Ru, (p-cymene){CH₂=C(ⁱBu)(CH₂)₂
CH=CH₂}Ru, (p-cymene){CH₂=C(ˢᵉᶜBu)(CH₂)₂
CH=CH₂}Ru, (p-cymene){CH₂=C(ᵗBu)(CH₂)₂
CH=CH₂}Ru, (p-cymene){CH₂=C(n-pentyl)(CH₂)₂
CH=CH₂}Ru, (p-cymene){CH₂=C(iso-pentyl)(CH₂)₂
CH=CH₂}Ru, (p-cymene){CH₂=C(sec-pentyl)(CH₂)₂
CH=CH₂}Ru, (p-cymene){CH₂=C(neo-pentyl)(CH₂)₂
CH=CH₂}Ru, (p-cymene){CH₂=C(tert-pentyl)(CH₂)₂
CH=CH₂}Ru, and (p-cymene){CH₂=C(3-pentyl)(CH₂)₂
CH=CH₂}Ru, and the ruthenium compound may include one member selected from the group consisting of, for example, (p-cymene) (1,3-butadiene)Ru, (p-cymene) (iso-prene)Ru, (p-cymene) (2,5-dimethyl-1,3-hexadiene)Ru, and (p-cymene) (1,5-hexadiene)Ru, but may not be limited thereto.

In accordance with a second aspect of the present disclosure, there is provided a method for preparing a ruthenium compound, including reacting a mixture including a [RuX₂(p-cymene)]₂ compound represented by the following Chemical Formula 2, a carbonate salt of an alkali metal represented as M₂CO₃, and a diene neutral ligand represented by the following Chemical Formula 3 in an organic solvent including a primary alcohol or secondary alcohol having 5 or less carbon atoms, as shown in the following Reaction Formula 1, to obtain a ruthenium compound represented by the following Chemical Formula 1:

[Chemical Formula 1]

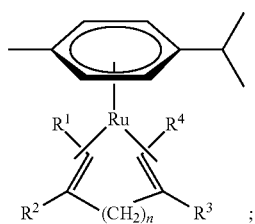

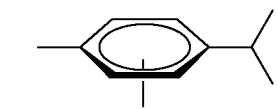

[Chemical Formula 2]

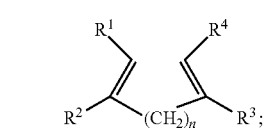

[Chemical Formula 3]

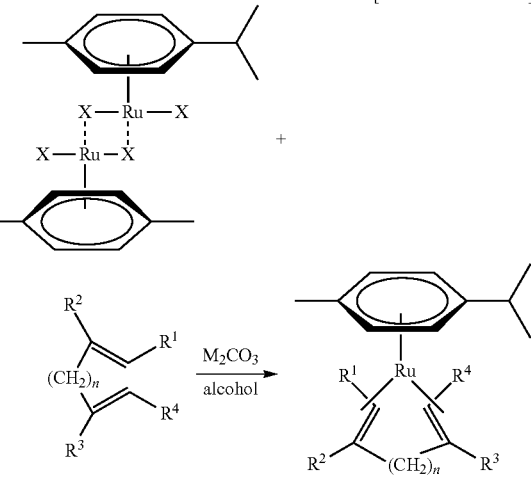

[Reaction Formula 1]

in the above Formulas,
M includes Li, Na, or K,
X includes Cl, Br, or I,
each of R¹ to R⁴ independently includes H, or a linear or branched $C_{1-5}$ alkyl group, and
n is an integer of from 0 to 3.

In an exemplary embodiment of the present disclosure, the reaction to obtain the ruthenium compound represented by Chemical Formula 1 may be a reaction under reflux, but may not be limited thereto.

In an exemplary embodiment of the present disclosure, the organic solvent may include a primary alcohol or secondary alcohol having 5 or less carbon atoms, but may not be limited thereto.

In an exemplary embodiment of the present disclosure, the primary alcohol or secondary alcohol having 5 or less carbon atoms may act as a solvent and also act as a reducing agent. Therefore, the ruthenium compound according to the present disclosure can be prepared through an economical and simple process which does not require a separate reducing agent.

In an exemplary embodiment of the present disclosure, the primary alcohol or secondary alcohol may include a member selected from the group consisting of methanol, ethanol, n-propyl alcohol, iso-propyl alcohol, n-butanol, iso-butanol, n-pentanol, iso-pentanol, and combinations thereof, but may not be limited thereto.

In an exemplary embodiment of the present disclosure, the [RuX₂(p-cymene)]₂ compound represented by the above Chemical Formula 2 may be prepared by a method which includes reacting a mixture including a ruthenium trichloride hydrate (RuX$_3$.nH$_2$O) and a-terpinene represented by the following Chemical Formula 4 or γ-terpinene represented by the following Chemical Formula 5 in an organic solvent, as shown in the following Reaction Formula 2, but may not be limited thereto. Herein, instead of the α-terpinene or γ-terpinene, β-terpinene, δ-terpinene, α-phellandrene, β-phellandrene, or isomers thereof may be used. In an exemplary embodiment of the present disclosure, the reaction to obtain the [RuX$_2$(p-cymene)]$_2$ compound represented by Chemical Formula 2 may be a reflux reaction, but may not be limited thereto.

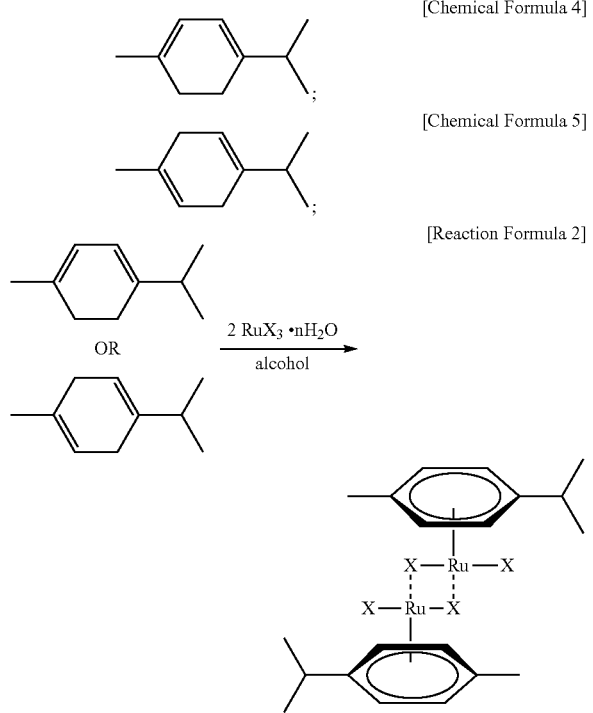

[Chemical Formula 4]

[Chemical Formula 5]

[Reaction Formula 2]

in the above Formulas,

X includes Cl, Br, or I, and n is 0 or an integer of 10 or less.

In order to prepare the [RuX$_2$(p-cymene)]$_2$ compound, the ruthenium trihalide hydrate (RuX$_3$.nH$_2$O) and α-terpinene represented by the above Chemical Formula 4 or γ-terpinene represented by the above Chemical Formula 5 are added to an organic solvent including an alcohol and then dissolved and reacted therein. Further, α-terpinene represented by the above Chemical Formula 4 or γ-terpinene represented by the above Chemical Formula 5 are added thereto and reacted therein, so that the [RuX$_2$(p-cymene)]$_2$ compound can be prepared. Then, a mixture including the as-prepared [RuX$_2$(p-cymene)]$_2$ compound; a carbonate salt (M$_2$CO$_3$) of an alkali metal or an alkali metal; and the diazadiene ligand is reacted under reflux as shown in the above Reaction Formula 1 or 2, so that the ruthenium compound represented by the above Chemical Formula 1 is prepared.

In accordance with a third aspect of the present disclosure, there is provided a precursor composition for depositing a ruthenium-containing film or thin film, including the ruthenium compound according to the first aspect of the present disclosure. The ruthenium-containing film may be a thin film having a thickness of nanometers, but may not be limited thereto.

In accordance with a fourth aspect of the present disclosure, there is provided a method for depositing a ruthenium-containing film or thin film, including forming a ruthenium-containing film or thin film by using the precursor composition for depositing a ruthenium-containing film or thin film according to the third aspect of the present disclosure. The ruthenium-containing film may be a thin film having a thickness of nanometers, but may not be limited thereto.

In an exemplary embodiment of the present disclosure, the method for depositing a ruthenium-containing film or thin film may include depositing the precursor composition for depositing a ruthenium-containing film or thin film on a substrate placed in a deposition chamber to form a ruthenium-containing film or thin film, but may not be limited thereto. The method for depositing a film may be performed using a method and an apparatus known in the art and, if necessary, also using an additional reaction gas.

In an exemplary embodiment of the present disclosure, the depositing of a film may be performed by a metal organic chemical vapor deposition (MOCVD) method or an atomic layer deposition (ALD) method, but may not be limited thereto. The metal organic chemical vapor deposition (MOCVD) method or the atomic layer deposition (ALD) method may be performed using a deposition apparatus, deposition conditions, an additional reaction gas, and the like known in the art.

A ruthenium compound in accordance with an exemplary embodiment of the present disclosure may is a complex in which ruthenium central metal is bonded to a ligand by weak coordinate bonds, and, thus, the ligand is easily degraded at a relatively low temperature, so that a deposition temperature can be lowered. Further, p-cymene and a diene neutral ligand separated from the ruthenium central metal are easily removed from the reaction chamber by vacuum evacuation, and, thus, impurities such as carbon, nitrogen, oxygen, and the like may not remain on the deposited film.

In an exemplary embodiment of the present disclosure, the depositing of a film may be performed by a metal organic chemical vapor deposition (MOCVD) method or an atomic layer deposition (ALD) method, but may not be limited thereto.

Detailed descriptions of parts of the third aspect and the fourth aspect of the present disclosure, which overlap with those of the first aspect and the second aspect of the present disclosure, are omitted hereinafter, but the descriptions of the first aspect and the second aspect of the present disclosure may be identically applied to the third aspect and the fourth aspect of the present disclosure, even though they are omitted hereinafter.

Hereinafter, the present disclosure will be explained in more detail with reference to Examples. However, the following Examples are illustrative only for better understanding of the present disclosure but do not limit the present disclosure.

MODE FOR CARRYING OUT THE INVENTION

<Preparation Example 1> Preparation of [RuCl$_2$(p-cymene)]$_2$ 27 g (0.13 mol, 1 equivalent) of ruthenium trichloride hydrate (RuCl$_3$.nH$_2$O) was dissolved by 200 mL of ethanol (C$_2$H$_5$OH) in a flame-dried 500 mL Schlenk flask, and 35.4 g (0.26 mol, 2 equivalents) of α-terpinene was slowly added to this solution at room temperature, and the reaction was completed after reflux of the mixed solution for 15 hours.

A dark brown solid obtained by the filtration after completion of the reaction was washed three times with 50 mL of n-hexane ($C_6H_{14}$) and then vacuum-dried, so that a reddish brown solid compound $RuCl_2$(p-cymene))$_2$ was obtained.

<Example 1> Preparation of (p-cymene)(1,3-butadiene)Ru 20 g (0.032 mol, 1 equivalent) of the $RuCl_2$(p-cymene))$_2$ prepared in Preparation Example 1 and 20.78 g (0.196 mol, 6 equivalents) of $Na_2CO_3$ were mixed with 400 mL of 2-propanol in a flame-dried 500 mL Schlenk flask to prepare a suspension, and the suspension was stirred for 2 hours. Then, 44.2 g (0.816 mol, 25 equivalents) of 1,3-butadiene was slowly mixed by bubbling with the suspension stirred for 2 hours, and the reaction was completed after reflux of the mixed solution for 2 days.

After completion of the reaction, the solvent and volatile by-products were removed under reduced pressure, and then extraction was performed using 500 mL of n-hexane. A filtrate was obtained by filtering the n-hexane extract through a Celite pad and a glass frit, and the solvent was removed from the filtrate under reduced pressure, and then, the filtrate was distillated under reduced pressure, so that 4.2 g (yield of 22.2%) of a yellow liquid compound represented by the following Chemical Formula 6 was obtained:

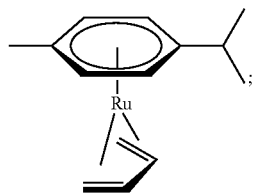

[Chemical Formula 6]

Boiling Point (bp): 95° C. (0.3 torr);
Elemental analysis calcd for ($C_{14}H_{20}Ru$): C 58.11, H 6.97; found C 56.95, H 6.80; and
$^1$H-NMR (400 MHz, $C_6D_6$, 25° C.) δ 5.035, 4.977 (m, 4H, $C_6H_4$); 4.733 (m, 2H, $CH_2$=CHCH=$CH_2$); 2.206 (septet, 1H, $CH(CH_3)_2$); 1.852 (s, 3H, $CH_3$); 1.031 (d, 6H, CH$(CH_3)_2$); 0.333 (d, 4H, $CH_2$=CHCH=$CH_2$).

<Example 2> Preparation of (p-cymene)(isoprene)Ru 30 g (0.049 mol, 1 equivalent) of the $RuCl_2$(p-cymene)]$_2$ prepared in Preparation Example 1 and 31.2 g (0.294 mol, 6 equivalents) of $Na_2CO_3$ were mixed with 400 mL of 2-propanol in a flame-dried 1,000 mL Schlenk flask to prepare a suspension, and the suspension was stirred for 2 hours. Then, 16.7 g (0.245 mol, 5 equivalents) of isoprene was slowly added and mixed with the above suspension stirred for 2 hours, and the reaction was completed after reflux of the mixed solution for 15 hours.

After completion of the reaction, a solvent and volatile by-products were removed under reduced pressure, and then extraction was performed using 500 mL of n-hexane. A filtrate was obtained by filtering the n-hexane extract through a Celite pad and a glass frit, and the solvent was removed from the filtrate under reduced pressure, and then, the filtrate was distillated under reduced pressure, so that 16.2 g (yield of 54.5%) of a yellow solid compound represented by the following Chemical Formula 7 was obtained:

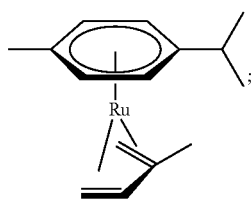

[Chemical Formula 7]

Boiling Point (bp): 97° C. (0.3 torr);
Melting Point (mp): 48° C.;
Elemental analysis calcd for ($C_{15}H_{22}Ru$): C 59.38, H 7.31; found C 59.60, H 7.56; and
$^1$H-NMR (400 MHz, $C_6D_6$, 25° C.) δ 5.125, 4.915, 4.706 (m, 4H, $C_6H_4$); 4.680 (m, 1H, $CH_2$=CHC($CH_3$)=$CH_2$); 2.307 (septet, 1H, $CH(CH_3)_2$); 1.967 (s, 3H, $CH_2$=CHC($CH_3$)=$CH_2$); 1.886, 0.381 (m, 2H, $CH_2$=CHC($CH_3$)=$CH_2$); 1.818, 0.195 (m, 2H, $CH_2$=CHC($CH_3$)=$CH_2$); 1.779 (s, 3H, $CH_3$); 1.111 (t, 6H, $CH(CH_3)_2$).

<Example 3> Preparation of (p-cymene)(2,5-dimethyl-1,3-hexadiene)Ru 25 g (0.040 mol, 1 equivalent) of the $RuCl_2$(p-cymene)]$_2$ prepared in Preparation Example 1 and 25.9 g (0.245 mol, 6 equivalents) of $Na_2CO_3$ were mixed with 400 mL of 2-propanol in a flame-dried 500 mL Schlenk flask to prepare a suspension, and the suspension was stirred for 2 hours. Then, 18.7 g (0.163 mol, 4 equivalents) of 2,5-dimethyl-2,4-hexadiene was slowly added and mixed with the suspension stirred for 2 hours, and the reaction was completed after reflux of the mixed solution for 15 hours.

After completion of the reaction, a solvent and volatile by-products were removed under reduced pressure, and then extraction was performed using 500 mL of n-hexane. A filtrate was obtained by filtering the n-hexane extract through a Celite pad and a glass frit, and the solvent was removed from the filtrate under reduced pressure, and then, the filtrate was distillated under reduced pressure, so that 16.5 g (yield of 57%) of a yellow liquid compound represented by the following Chemical Formula 8 was obtained:

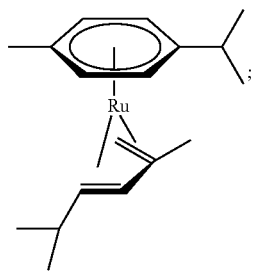

[Chemical Formula 8]

Boiling Point (bp): 110° C. (0.3 torr);
Elemental analysis calcd for ($C_{18}H_{28}Ru$): C 62.58, H 8.17; found C 55.73, H 7.84; and
$^1$H-NMR (400 MHz, $C_6D_6$, 25° C.) δ 5.030, 4.863, 4.591, 4.428 (m, 4H, $C_6H_4$); 4.411 (m, 1H, $CH_2$=C($CH_3$)CH=CHCH($CH_3$)$_2$); 2.413 (septet, 1H, $CH(CH_3)_2$); 1.994

(m, 6H, CH(CH$_3$)$_2$); 1.787, 0.287 (m, 2H, CH$_2$=C(CH$_3$)CH=CHCH(CH$_3$)$_2$); 1.448 (m, 1H, CH$_2$=C(CH$_3$)CH=CHCH(CH$_3$)$_2$); 1.229 (d, 6H, CH$_2$=C(CH$_3$)CH=CHCH(CH$_3$)$_2$), 1.182 (s, 3H, CH$_3$); 1.162 (s, 3H, CH$_2$=C(CH$_3$)CH=CHCH(CH$_3$)$_2$); 0.530 (t, 1H, CH$_2$=C(CH$_3$)CH=CHCH(CH$_3$)$_2$).

<Example 4> Preparation of (p-cymene)(1,5-hexadiene)Ru 30 g (0.049 mol, 1 equivalent) of the RuCl$_2$(p-cymene)]$_2$ prepared in Preparation Example 1 and 31.1 g (0.294 mol, 6 equivalents) of Na$_2$CO$_3$ were mixed with 400 mL of 2-propanol in a flame-dried 1,000 mL Schlenk flask to prepare a suspension, and the suspension was stirred for 2 hours. Then, 16.10 g (0.196 mol, 4 equivalents) of 1,5-hexadiene was slowly added and mixed with the suspension stirred for 2 hours, and the reaction was completed after reflux of the mixed solution for 15 hours.

After completion of the reaction, a solvent and volatile by-products were removed under reduced pressure, and then extraction was performed using 500 mL of n-hexane. A filtrate was obtained by filtering the n-hexane extract through a Celite pad and a glass frit, and the solvent was removed from the filtrate under reduced pressure, and then, the filtrate was distillated under reduced pressure, so that 17.5 g (yield of 56%) of a yellow liquid compound represented by the following Chemical Formula 9 was obtained:

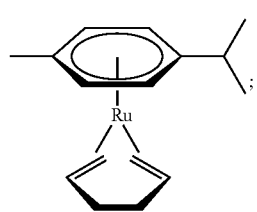

[Chemical Formula 9]

Boiling Point (bp): 105° C. (0.3 torr);
Elemental analysis calcd for (C$_{16}$H$_{24}$Ru): C 60.54, H 7.62; found C 59.64, H 7.41; and
$^1$H-NMR (400 MHz, C$_6$D$_6$, 25° C.) δ 4.990, 4.831, 4.689 (m, 4H, C$_6$H$_4$); 4.667 (m, 2H, CH$_2$=CHCH$_2$CH$_2$CH=CH$_2$); 4.361, 0.802 (m, 4H, CH$_2$=CHCH$_2$CH$_2$CH=CH$_2$); 2.334 (septet, 1H, CH(CH$_3$)$_2$); 2.005 (s, 3H, CH$_3$); 1.395 (d, 6H, CH(CH$_3$)$_2$); 1.150 (m, 4H, CH$_2$=CHCH$_2$CH$_2$CH=CH$_2$).

<Test Example 1> Thermogravimetric Analysis and Differential Scanning Calorimetry Test In order to analyze basic thermal characteristics of the ruthenium compounds prepared in Example 1 to Example 4, thermogravimetric analysis (TGA) and differential scanning calorimetry (DSC) were conducted. Herein, about 5 mg of each sample was placed in an alumina sample container, and then, a measurement was conducted up to 500° C. at a temperature-increase rate of 10° C./min, and the measurement results were as shown in FIG. 1 through FIG. 8.

As can be seen from FIG. 1 through FIG. 8, all the ruthenium compounds represented by Chemical Formula 6 through Chemical Formula 9 of the present disclosure were sharply decreased in mass at a temperature of from 150° C. to 250° C. according to the TGA graphs, and a temperature $T_{1/2}$ when reaching ½ of the initial weight of each sample during the decrease in weight depending on the temperature was in the range of from 217° C. to 228° C. Further, according to the DSC graphs, the ruthenium compounds represented by Chemical Formula 6 through Chemical Formula 9 of the present disclosure showed endothermic peaks due to degradation of each of the compounds at 320° C., 336° C., 357° C., and 281° C., respectively.

Figure 9:
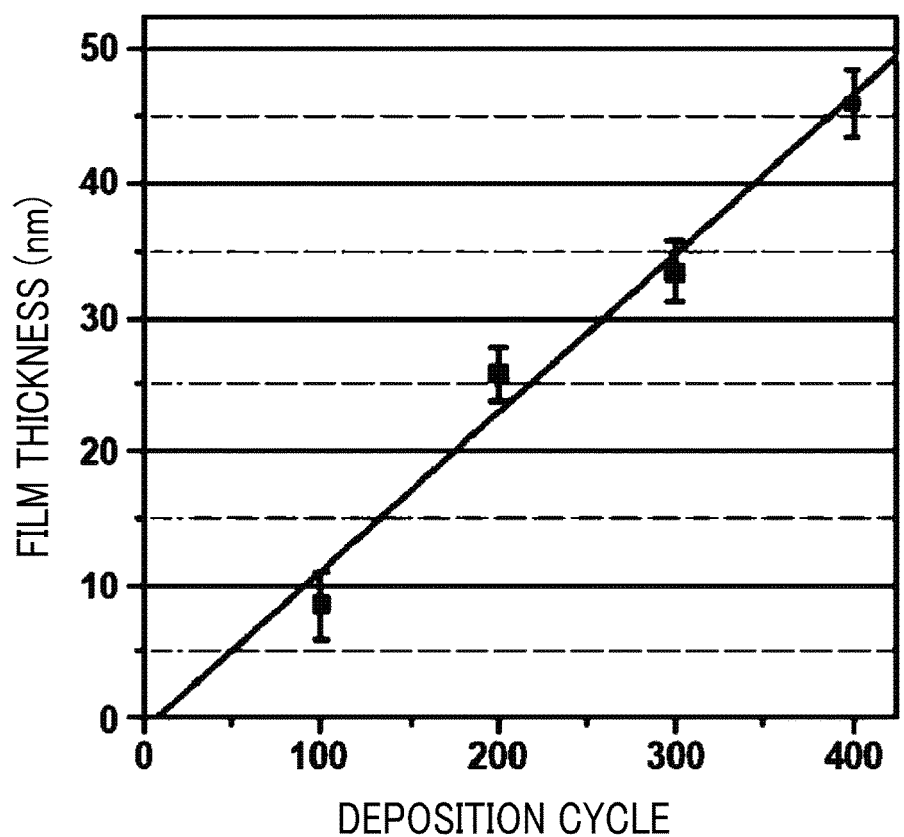
FIG. 9 is a graph showing a relationship between the number of times of atomic layer deposition cycle and a thickness of the ruthenium-containing film formed on a silicon oxide ($SiO_2$) substrate in accordance with Example 5 of the present disclosure.
Figure 10:
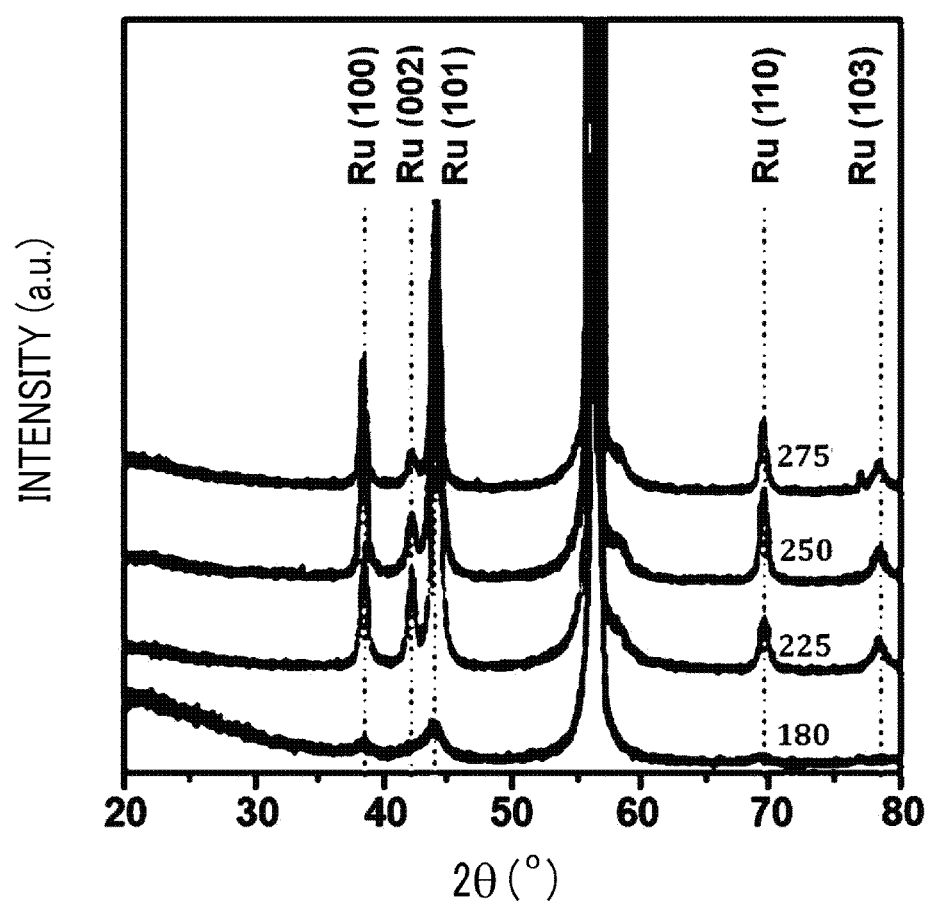
FIG. 10 shows the result of X-ray diffraction analysis of the ruthenium-containing film formed on the silicon oxide substrate in accordance with Example 5 of the present disclosure.

<Example 5> Formation of Ruthenium-Containing Film by Atomic Layer Deposition Method Using (p-cymene)(isoprene)Ru Compound Gas Prepared in Example 2 and Oxygen Gas An evaluation of a film formed by an atomic layer deposition method using the (p-cymene)(isoprene)Ru compound represented by Chemical Formula 7 prepared in Example 2 as a precursor was conducted. A wafer including a silicon substrate coated with a silicon oxide (SiO$_2$) film to a thickness of 100 nm was used as a substrate for deposition. Herein, a temperature of the substrate was controlled in the range of from 180° C. to 275° C., and the precursor was placed in a stainless steel container and then vaporized by heating the container at a temperature of 85° C. The ruthenium precursor gas prepared in Example 2 which was transported with a carrier gas in a Lucida D-100 atomic layer deposition apparatus manufactured by NCD Co., Ltd and oxygen (O$_2$) gas diluted in nitrogen (N$_2$) gas to a concentration of 20 vol. % were alternately brought into contact with the substrate placed in the atomic layer deposition chamber. A ruthenium-containing film was formed at a substrate temperature of 275° C. by repeating an atomic layer deposition cycle including the supply of the Ru precursor prepared in Example 2 for 5 seconds→the supply of N$_2$ gas for 10 seconds→the supply of O$_2$ gas for 3 seconds→the supply of N$_2$ gas for 10 seconds from 100 times to 400 times. A cross section of the formed ruthenium-containing films was measured using a scanning electron microscope, and a thickness thereof was as shown in FIG. 9. XRD patterns of ruthenium-containing films formed at the various substrate temperatures were measured using an X-ray Diffractometer (XRD), as shown in FIG. 10. An electrical resistivity of a ruthenium-containing film formed to a thickness of 25 nm by repeating the atomic layer deposition cycle 200 times was 42 μΩ·cm, and, thus, it could be formed that the formed ruthenium-containing film had a very excellent electrical conductivity.

As a result of comparison between the number of times of the atomic layer deposition gas supply cycle and a thickness of a ruthenium-containing film with reference to FIG. 9, it could be seen that in the atomic layer deposition method using the ruthenium compound prepared in Example 2 on the SiO$_2$ substrate, the film growth per gas supply cycle was high (~0.12 nm/cycle) and it was difficult to nucleate, and, thus, an incubation cycle was very short (~7 cycles) even on a surface of the silicon oxide unfavorable for an initial film growth. Further, as can be seen from FIG. 10, it could be seen that a crystalline Ru metal film was formed at a substrate temperature of 225° C. or more. It is generally known that a metal film with a higher crystallinity has a higher electrical conductivity.

Figure 11:
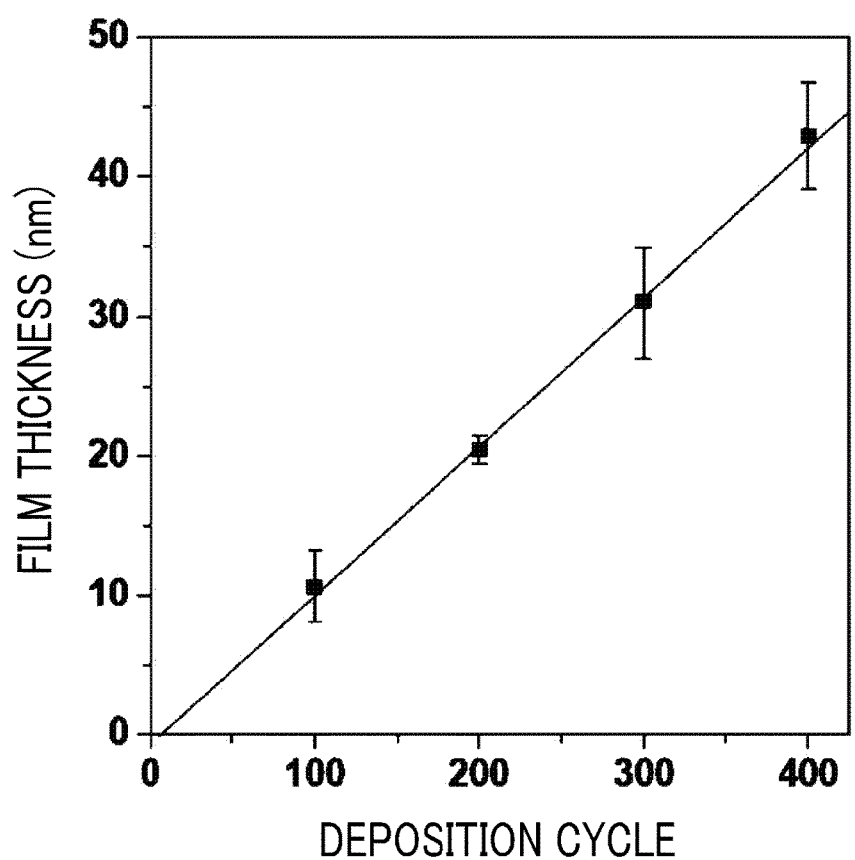
FIG. 11 is a graph showing a relationship between the number of times of atomic layer deposition cycle and a thickness of the ruthenium-containing film formed in accordance with Example 6 of the present disclosure.
Figure 12:
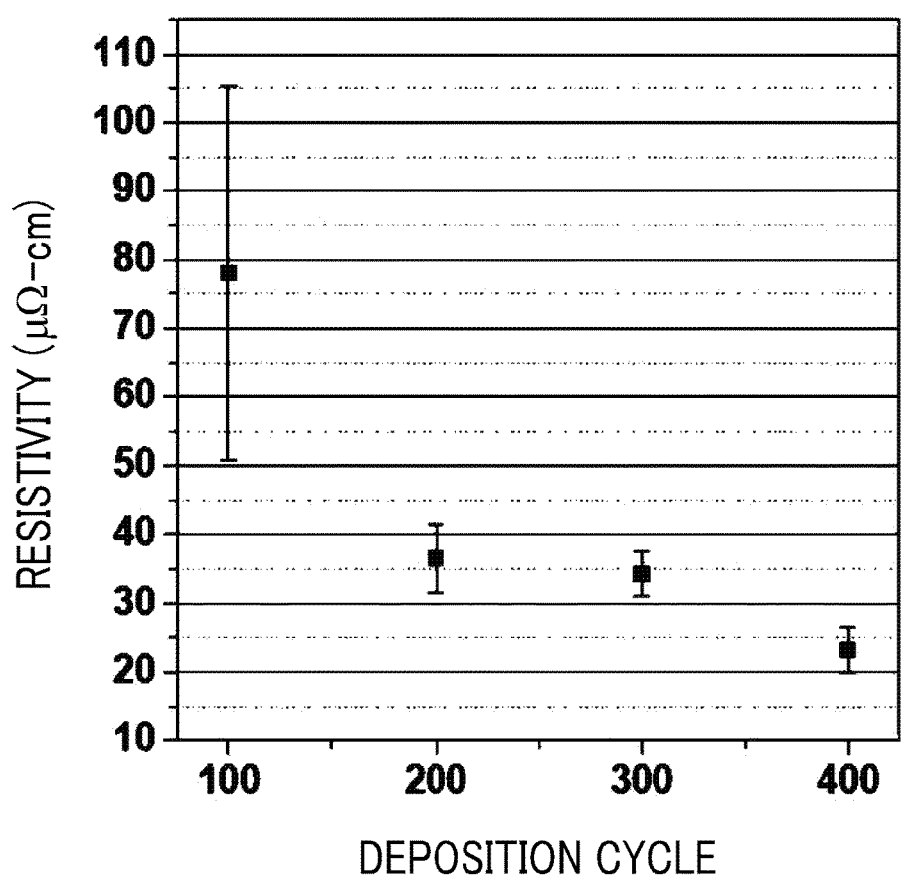
FIG. 12 is a graph showing an electrical resistivity of the ruthenium-containing film in accordance with Example 6 of the present disclosure.
Figure 13:
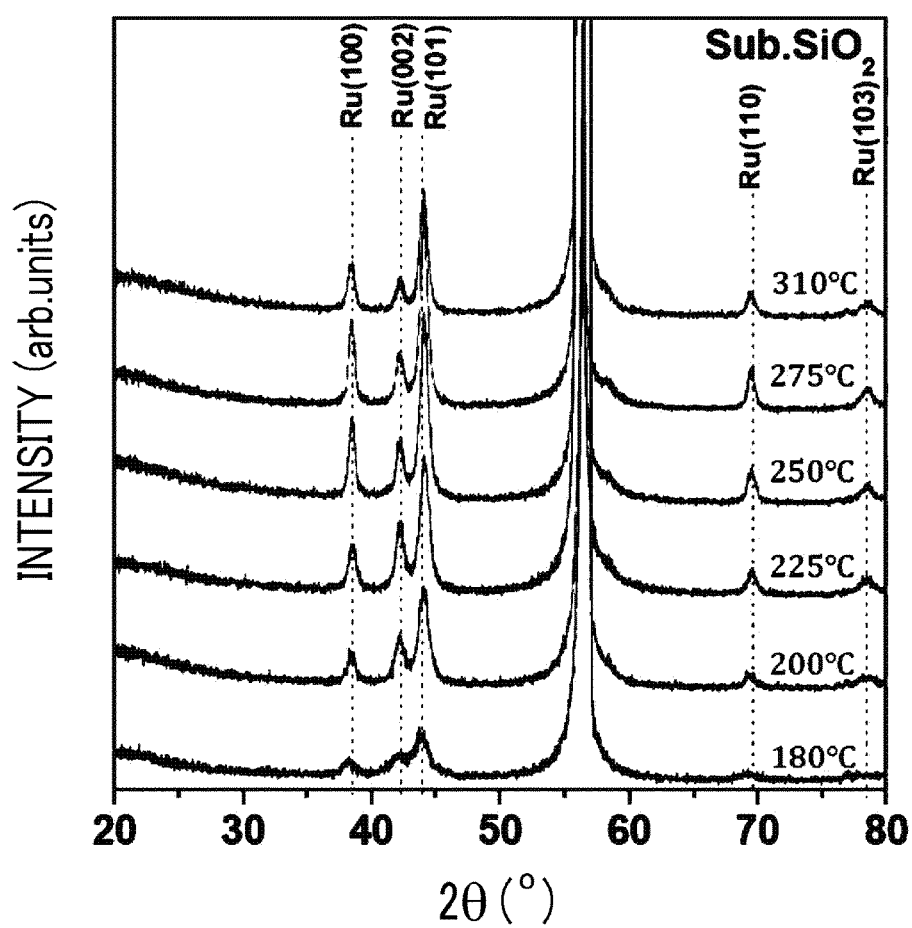
FIG. 13 shows the result of X-ray diffraction analysis of the ruthenium-containing film in accordance with Example 6 of the present disclosure.

<Example 6> Formation of Ruthenium-Containing Film by Atomic Layer Deposition Method Using (p-cymene)(1,3-butadiene)Ru Compound Gas Prepared in Example 1 and Oxygen Gas An evaluation of a film formed by an atomic layer deposition method using the (p-cymene)(1,3-butadiene)Ru compound represented by Chemical Formula 6 prepared in Example 1 as a precursor was conducted. A wafer including a silicon substrate coated with a silicon oxide ($SiO_2$) film to a thickness of 100 nm was used as a substrate for deposition. Herein, a temperature of the substrate was controlled in the range of from 180° C. to 310° C., and the precursor was placed in a stainless steel container and then vaporized by heating the container at a temperature of 84° C. The ruthenium precursor gas transported with a carrier gas in a Lucida D-100 atomic layer deposition apparatus manufactured by NCD Co., Ltd and oxygen ($O_2$) gas diluted in nitrogen ($N_2$) gas to a concentration of 20 vol. % were alternately brought into contact with the substrate placed in an atomic layer deposition chamber. A ruthenium-containing film was formed at a substrate temperature of 225° C. by repeating an atomic layer deposition cycle including the supply of the Ru precursor prepared in Example 1 for 5 seconds→the supply of $N_2$ gas for 10 seconds→the supply of $O_2$ gas for 1 second→the supply of $N_2$ gas for 10 seconds from 100 times to 400 times. A cross section of the formed ruthenium-containing film was measured using a scanning electron microscope, and a thickness thereof was as shown in FIG. 11. Electrical resistivities of the ruthenium-containing films were as shown in FIG. 12. XRD patterns of ruthenium-containing films formed at various substrate temperatures were measured using an X-ray Diffractometer (XRD), as shown in FIG. 13.

As a result of comparison between the number of times of atomic layer deposition gas supply cycle and a thickness of a ruthenium-containing film with reference to FIG. 11, it could be seen that in the atomic layer deposition method using the ruthenium compound prepared in Example 1 on the $SiO_2$ substrate, the film growth per gas supply cycle was high (~0.106 nm/cycle) and it was difficult to nucleate, and, thus, an incubation cycle was very short (~7 cycles) even on a surface of the silicon oxide unfavorable for initial film growth. Further, as can be seen from FIG. 12, it could be seen that a film formed to a thickness of 20 nm or more by repeating the atomic layer deposition cycle 200 times had a high electrical conductivity and its resistivity was lower than 40 μΩ·cm, and, thus, it could be seen that the formed film had a very excellent electrical conductivity. Furthermore, as can be seen from FIG. 13 that a crystalline Ru metal film was formed at a substrate temperature of 200° C. or more. It is generally known that a metal film with a higher crystallinity has a higher electrical conductivity.

Moreover, a surface of a ruthenium-containing film formed to a thickness of 20 nm was observed using an atomic force microscope, and it was found that the surface of the ruthenium-containing film had a surface unevenness of 1.36 nm, and, thus, it could be seen that the obtained film was very smooth.

<Example 7> Formation of Ruthenium-Containing Film by Atomic Layer Deposition Method Using (p-cymene)(2,5-dimethyl-1,3-hexadiene)Ru Compound Gas Prepared in Example 3 and Oxygen Gas An evaluation of a film formed by an atomic layer deposition method using the (p-cymene)(2,5-dimethyl-1,3-hexadiene)Ru compound and represented by Chemical Formula 8 prepared in Example 3 as a precursor was conducted. A wafer including a silicon substrate coated with a silicon oxide ($SiO_2$) film to a thickness of 100 nm was used as a substrate for deposition. Herein, a temperature of the substrate was controlled in the range of from 180° C. to 310° C., and the precursor was placed in a stainless steel container and then vaporized by heating the container at a temperature of 90° C. The ruthenium precursor gas transported with a carrier gas in a Lucida D-100 atomic layer deposition apparatus manufactured by NCD Co., Ltd and oxygen ($O_2$) gas diluted in nitrogen ($N_2$) gas to a concentration of 20 vol. % were alternately brought into contact with the substrate placed in an atomic layer deposition chamber. A ruthenium-containing film was formed at a substrate temperature of 225° C. by repeating an atomic layer deposition cycle including the supply of the Ru precursor prepared in Example 3 for 5 seconds→the supply of $N_2$ gas for 10 seconds→the supply of $O_2$ gas for 2 seconds→the supply of $N_2$ gas for 10 seconds.

As a result of comparison between the number of times of atomic layer deposition gas supply cycle and a thickness of a ruthenium-containing film, the film growth per gas supply cycle was 0.096 nm/cycle and an incubation cycle was ~12 cycles at a substrate temperature of 225° C. An electrical resistivity of a ruthenium-containing film formed at a substrate temperature of 225° C. was in the range of from 55 μΩ·cm to 65 μΩ·cm. Further, a surface of a ruthenium-containing film formed to a thickness of 20 nm was observed using an atomic force microscope, and it was found that the surface of the ruthenium-containing film had a surface unevenness of 1.35 nm, and, thus, it could be seen that the obtained film was very smooth.

Particularly, a terpinene compound used as a starting material in Example 1 is commercially available and can be easily obtained in a large quantity of several tens kg or several hundreds kg. Therefore, the ruthenium compound of the present disclosure including the ruthenium compounds of Example 1 to Example 4 synthesized from the terpinene can be easily mass-produced from the commercially available source material and thus is highly favorable for industrial use for the purpose of depositing a Ru-containing film.

Further, in case of forming a ruthenium-containing film by an atomic layer deposition method using the ruthenium compound according to the present disclosure, a ruthenium-containing film having a high electric conductivity with a smooth surface can be formed. The atomic layer deposition method using the ruthenium compound according to the present disclosure enables fast initial film growth and particularly film growth per gas supply cycle to be in the range of from 0.096 nm/cycle to 0.12 nm/cycle which is about 2 or more times faster than the conventionally known atomic layer deposition method, and, thus, it can reduce a time to form a ruthenium-containing film to a required thickness by half as compared with the conventionally known atomic layer deposition method. If the ruthenium compound according to the present disclosure is applied to a semiconductor production process for preparing a ruthenium-containing film, it is expected that productivity of a film forming device will be doubled.

The above description of the present disclosure is provided for the purpose of illustration, and it would be understood by those skilled in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A ruthenium compound, represented by the following Chemical Formula 1:

[Chemical formula 1]

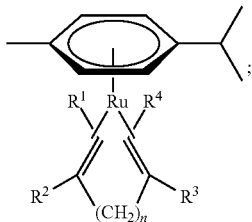

wherein in the above Chemical Formula 1, each of $R^1$ to $R^4$ independently is H, or a member selected from the group consisting of: methyl group; ethyl group; iso-propyl group; and, tert-butyl group; and n is an integer of from 0 to 3.

2. The ruthenium compound of claim 1, wherein the ruthenium compound includes a member selected from the group consisting of (p-cymene)(1,3-butadiene)Ru, (p-cymene)(isoprene)Ru, (p-cymene)(2,5-dimethyl-1,3-hexadiene)Ru, and (p-cymene)(1,5-hexadiene)Ru.

3. A method for preparing a ruthenium compound of claim 1, comprising:

reacting a mixture including a $[RuX_2(p\text{-cymene})]z$ compound represented by the following Chemical Formula 2, a carbonate salt of an alkali metal represented as $M_2CO_3$, and a diene neutral ligand represented by the following Chemical Formula 3 in an organic solvent including a primary alcohol or secondary alcohol having 5 or less carbon atoms, as shown in the following Reaction Formula 1, to obtain a ruthenium compound represented by the following Chemical Formula 1:

[Chemical Formula 1]

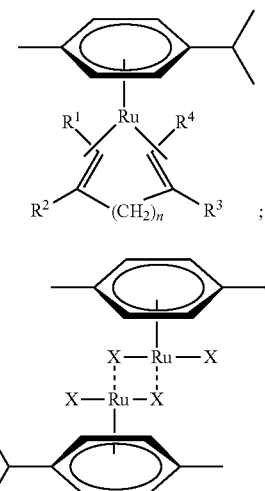

[Chemical Formula 2]

[Chemical Formula 3]

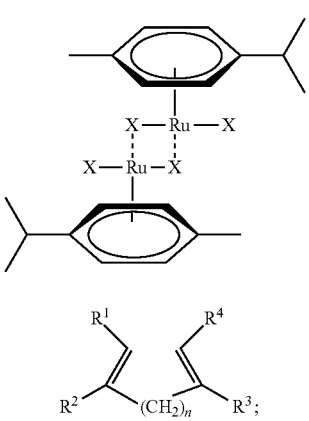

[Reaction Formula 1]

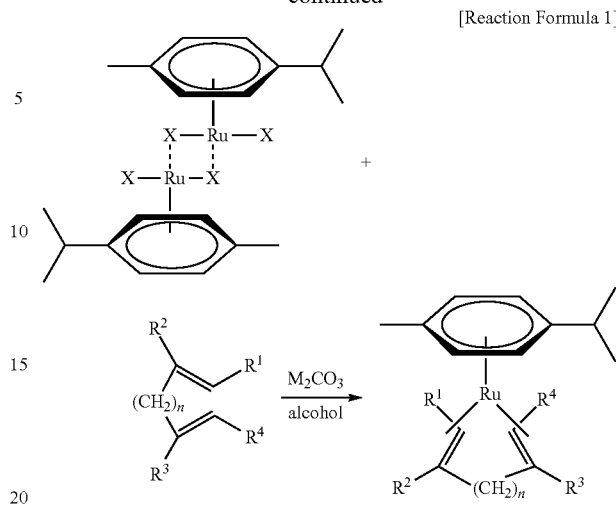

wherein in the above Formulas,

M includes Li, Na, or K,

X includes Cl, Br, or I, and $R^1$ to $R^4$, and n are the same as defined in claim 1.

4. The method for preparing a ruthenium compound of claim 3, wherein the primary alcohol or secondary alcohol includes a member selected from the group consisting of methanol, ethanol, n-propyl alcohol, iso-propyl alcohol, n-butanol, iso-butanol, n-pentanol, iso-pentanol, and combinations thereof.

5. A precursor composition for depositing a ruthenium-containing film, comprising a container including the ruthenium compound of claim 1.

6. A method for depositing a ruthenium-containing film, comprising: depositing the precursor composition of claim 5 to form a ruthenium-containing film.

7. The method for depositing a ruthenium-containing film of claim 6, wherein the precursor composition is deposited by a metal organic chemical vapor deposition (MOCVD) method or an atomic layer deposition (ALD) method.

8. A method for preparing a ruthenium compound of claim 2, comprising:

reacting a mixture including a $[RuX_2(p\text{-cymene})]_2$ compound represented by the following Chemical Formula 2, a carbonate salt of an alkali metal represented as $M_2CO_3$, and a diene neutral ligand represented by the following Chemical Formula 3 in an organic solvent including a primary alcohol or secondary alcohol having 5 or less carbon atoms, as shown in the following Reaction Formula 1, to obtain a ruthenium compound represented by the following Chemical Formula 1:

[Chemical Formula 1]

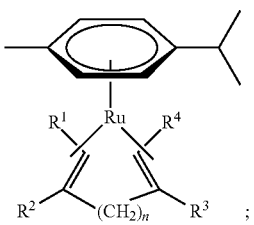

21
-continued

[Chemical Formula 2]

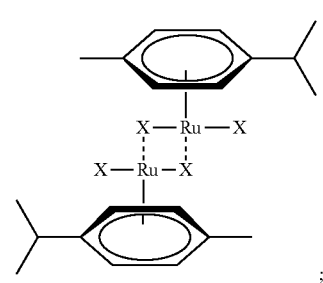

;

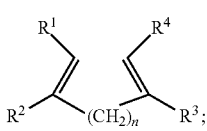

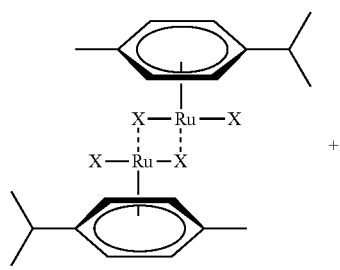

+

[Chemical Formula 3]

[Reaction Formula 1]

22
-continued

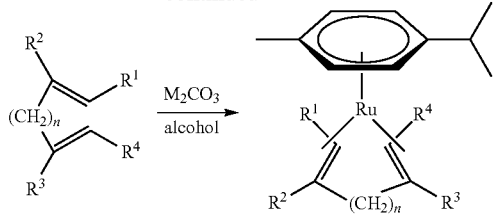

wherein in the above Formulas,
M includes Li, Na, or K,
X includes Cl, Br, or I, and
$R^1$ to $R^4$, and n are the same as defined in claim 1.

9. The method for preparing a ruthenium compound of claim 8, wherein the primary alcohol or secondary alcohol includes a member selected from the group consisting of methanol, ethanol, n-propyl alcohol, iso-propyl alcohol, n-butanol, iso-butanol, n-pentanol, iso-pentanol, and combinations thereof.

10. A precursor composition for depositing a ruthenium-containing film, comprising a container including the ruthenium compound of claim 2.

11. A method for depositing a ruthenium-containing film, comprising: depositing the precursor composition of claim 10 to form a ruthenium-containing film.

12. The method for depositing a ruthenium-containing film of claim 11, wherein the precursor composition is deposited by a metal organic chemical vapor deposition (MOCVD) method or an atomic layer deposition (ALD) method.

* * * * *